(12) United States Patent
Nakahama

(10) Patent No.: US 8,513,024 B2
(45) Date of Patent: Aug. 20, 2013

(54) METHOD OF DETECTING TARGET SUBSTANCE AND TARGET-SUBSTANCE DETECTION KIT

(75) Inventor: Kazumichi Nakahama, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 474 days.

(21) Appl. No.: 12/517,053

(22) PCT Filed: Feb. 4, 2009

(86) PCT No.: PCT/JP2009/052249
§ 371 (c)(1),
(2), (4) Date: May 29, 2009

(87) PCT Pub. No.: WO2009/107484
PCT Pub. Date: Sep. 3, 2009

(65) Prior Publication Data
US 2011/0033947 A1    Feb. 10, 2011

(30) Foreign Application Priority Data

Feb. 26, 2008    (JP) .................................. 2008-044422

(51) Int. Cl.
*G01N 27/00*    (2006.01)
(52) U.S. Cl.
USPC ........... 436/149; 436/150; 436/151; 436/531; 436/532; 436/533; 436/534; 435/180
(58) Field of Classification Search
None
See application file for complete search history.

(56) References Cited

U.S. PATENT DOCUMENTS

| 5,206,159 A | 4/1993 | Cohen et al. |
| 2007/0298510 A1 | 12/2007 | Imamura et al. |
| 2008/0241964 A1 | 10/2008 | Kaieda et al. |

FOREIGN PATENT DOCUMENTS

| JP | 2004-99844 A | 4/2004 |
| JP | 2007-263935 A | 10/2007 |
| JP | 2007-278748 A | 10/2007 |

OTHER PUBLICATIONS

Suzuki, et al. "Stimuli-sensitive core/shell template particles for immobilizing inorganic nanoparticles in the core", Colloid Polymer Science (2006) No. 284, pp. 1443-1451.
PCT International Search Report and Written Opinion of the International Searching Authority, mailed May 19, 2009, in PCT/JP2009/052249.

*Primary Examiner* — Robert Xu
(74) *Attorney, Agent, or Firm* — Fitzpatrick, Cella, Harper & Scinto

(57) ABSTRACT

Provided is a detection method for a target substance capable of enhancing detection sensitivity and quantitative property of a magnetic biosensor, while keeping monodispersity and dispersion stability of magnetic markers, including the steps of: reacting the target substance in a sample solution with a first target substance trapping member immobilized on a sensing element and with a second target substance trapping member immobilized on a gel particle to hold the gel particle on the sensing element; adjusting a magnetic marker precursor including the gel particle and a magnetic material precursor existing in the gel particle by bringing the magnetic material precursor into contact with the gel particle; synthesizing a magnetic material from the magnetic material precursor held on the gel particle, thereby adjusting the magnetic markers; and detecting the magnetic markers with the sensing element.

7 Claims, 4 Drawing Sheets

METHOD OF DETECTING TARGET SUBSTANCE AND TARGET-SUBSTANCE DETECTION KIT

TECHNICAL FIELD

The present invention relates to a method of detecting a target substance in a sample solution by using a magnetic marker.

BACKGROUND ART

Under a background of social conditions such as an aging society and spreads of a lifestyle-related illness in recent years, needs for an immunological test system with high sensitive and high quantitative property, which enables early detection and early treatment of illness, are increasing. As a candidate of the immunological test system described above, there is given a magnetic biosensor. The magnetic biosensor is a detection system for detecting a target substance in a sample solution by magnetically detecting the magnetic markers locating in a vicinity of a surface of a detection section.

As the magnetic biosensor, there are known a superconducting quantum interference device (SQUID), a hall effect device, a magneto-resistance effect device, a magnetic impedance device, and the like.

In order to achieve a magnetic biosensor with high sensitivity and excellent in the quantitative property, development of a magnetic marker having the following properties is demanded. That is, the magnetic marker is required to have (1) a small size and excellent monodispersity; (2) large saturated magnetization of each of the magnetic markers (magnetic material content is high); and (3) excellent dispersion stability. The property (1) affects an enhancement of the quantitative property of the target substance in the magnetic biosensor. Further, the property (2) affects an enhancement of detection sensitivity of the target substance, and the property (3) affects an enhancement of the quantitative property of the target substance.

However, in many cases, the above-mentioned three properties are in a trade-off relation, thereby being difficult to produce a magnetic marker which fulfills the all properties. Under the above-mentioned background, there is disclosed a magnetic marker including a nonmagnetic substance such as a polymeric compound having a relatively high degree of freedoms of a molecular design and selection, and a magnetic material. For example, Japanese Patent Application Laid-Open No. 2004-099844 discloses a technique of obtaining a magnetic marker by utilizing a miniemulsion polymerization method. Further, in p145 of Preprints of the 14th Polymeric Microspheres Symposium, there is disclosed a technique of obtaining a magnetic marker through utilization of soap-free emulsion polymerization. In addition, Colloid Polymer Science, (2006), No. 284, p1443-p1451 discloses a technique of obtaining a magnetic marker by synthesizing a magnetic material using as a template the gel particle.

However, in the magnetic biosensor applying those magnetic markers, there is a problem in that, in order to achieve a high sensitive detection, magnitude of saturated magnetization is insufficient. It is possible to enhance the saturated magnetization of the magnetic markers by increasing a magnetic material content of each of the magnetic markers. However, by doing so, due to the trade-off relation described above, monodispersity and dispersion stability of the magnetic markers are degraded, and hence the quantitative property of the magnetic biosensor may be impaired.

DISCLOSURE OF THE INVENTION

The present invention has been made in view of the above-mentioned problems, and has an object to provide a detection method capable of enhancing the detection sensitivity and quantitative property of the magnetic biosensor, while keeping the monodispersity and dispersion stability of the magnetic marker, and a detection kit.

As a result of extensive studies to solve the above-mentioned problems, the inventors have found that it is possible to achieve a magnetic biosensor which is excellent in high sensitivity and quantitative property, by synthesizing a magnetic material to obtain magnetic markers using the gel particle bonded in the vicinity of a surface of a detection section as a template, and further by magnetically detecting the magnetic markers.

That is, a first invention of the present invention relates to a detection method of detecting presence or absence of, or a concentration of a target substance in a sample solution through detection of presence or absence of, or a number of magnetic markers, comprising the steps of:

reacting the target substance in the sample solution with a first target substance trapping member immobilized on a sensing element and with a second target substance trapping member immobilized on a gel particle, and forming a composite material by bonding the first target substance trapping member and the second target substance trapping member through intermediation of the target substance, thereby holding the gel particle on the sensing element;

adjusting a magnetic marker precursor comprising the gel particle and a magnetic material precursor existing in the gel particle by bringing the magnetic material precursor into contact with the gel particle which is held on the sensing element through formation of the composite material;

synthesizing a magnetic material from the magnetic material precursor held on the gel particle, thereby adjusting the magnetic markers comprising the gel particle and the magnetic material existing in the gel particle; and detecting the presence or absence of, or the number of the magnetic markers with the sensing element.

Further, a second invention of the present invention relates to a kit for magnetically detect a target substance in a sample solution, comprising:

a sensing element on which a first target substance trapping member is immobilized;

a gel particle on which a second target substance trapping member; and a magnetic material precursor.

Further features of the present invention will become apparent from the following description of exemplary embodiments with reference to the attached drawings.

BEST MODE FOR CARRYING OUT THE INVENTION

Hereinafter, the present invention is described in detail.

A detection method according to the present invention relates to a method of detecting presence or absence of, or a concentration of a target substance in a sample solution through detection of presence or absence of, or a number of magnetic markers, comprising the steps of:

(1) reacting the target substance in the sample solution with a first target substance trapping member immobilized on a sensing element and with a second target substance trapping member immobilized on a gel particle, and forming a composite material by bonding the first target substance trapping member and the second target substance trapping member through intermediation of the target substance, thereby holding the gel particle on the sensing element;

(2) adjusting a magnetic marker precursor comprising the gel particle and a magnetic material precursor existing in the gel particle by bringing the magnetic material precursor into contact with the gel particle which is held on the sensing element through formation of the composite material in the step (1) (this step may be considered as a step of causing the gel particle to hold the magnetic material precursor);

(3) synthesizing a magnetic material from the magnetic material precursor held on the gel particle, thereby adjusting the magnetic markers comprising the gel particle and the magnetic material existing in the gel particle (this step may be considered as a step of adjusting the magnetic marker comprising the magnetic material containing the gel); and (4) detecting the presence or absence of, or the number of the magnetic markers with the sensing element.

In the step (1), an order of the reaction between the target substance and the first target substance trapping member, and the reaction between the target substance and the second target substance trapping member is not particularly limited, and the respective reactions may be performed with one reaction being first and another reaction being second, or the both reactions may be performed in duplicate (including partial duplication).

That is, as a first mode, the step (1) may comprise the steps of:

(1-i) reacting the target substance in the sample solution with the first target substance trapping member; and (1-ii) reacting the target substance bonded to the first target substance trapping member with the second target substance trapping member.

Further, as a second mode, the step (1) may comprise the steps of:

(1-i) reacting the target substance in the sample solution with the second target substance trapping member; and (1-ii) reacting the target substance bonded to the second target substance trapping member with the first target substance trapping member.

Figure 1:
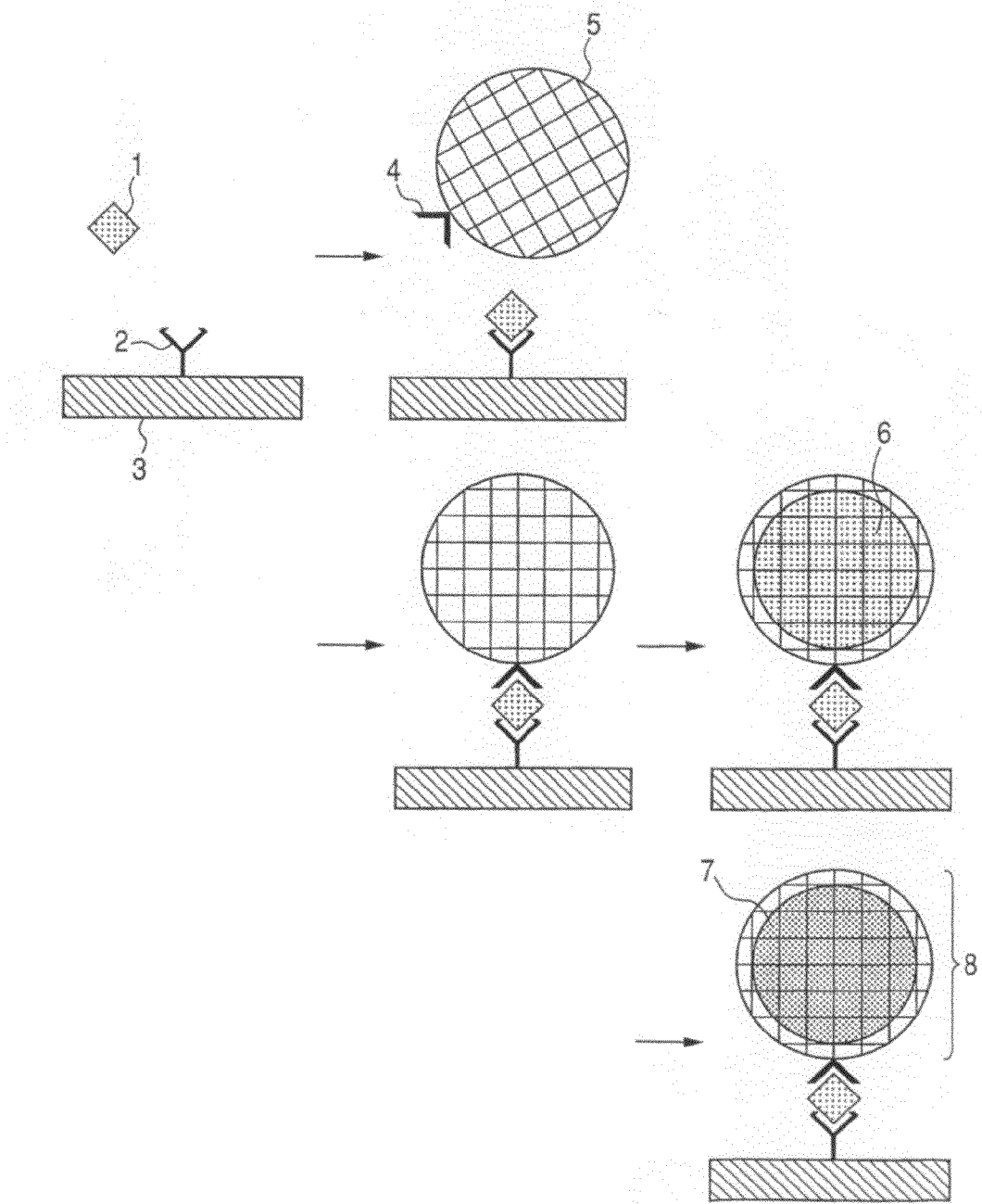
FIG. 1 is a schematic drawing illustrating a detection method according to the first mode of the present invention.

In a schematic drawing illustrated in FIG. 1, a detailed embodiment according to the first mode is described. In FIG. 1, first target substance trapping member 2 bonded (immobilized) on a sensing element 3 is reacted with a target substance 1 in a sample solution, and then a second target substance trapping member 4 bonded (immobilized) on a gel particle 5 is reacted with the target substance 1. Next, a magnetic material precursor 6 is charged into the sample solution to cause the gel particle 5 to absorb the magnetic material precursor 6.

In addition, a magnetic material 7 is synthesized from the magnetic material precursor 6 to obtain a magnetic marker 8 including the gel particle 5 and the magnetic material 7. Finally, the magnetic marker 8 is magnetically detected with the sensing element 3.

In order to achieve the magnetic biosensor with high sensitivity and excellent quantitative property, development of a magnetic marker having the following properties is demanded.

1. To have a small size and excellent monodispersity
2. To have large saturated magnetization of each of the magnetic markers (magnetic material content is high)
3. To have excellent dispersion stability However, in general, the above-mentioned three properties are in a trade-off relation, thereby being difficult to produce a magnetic marker that fulfills the all properties. For example, to enlarge the saturated magnetization, it is required to increase a magnetic material content of each of the magnetic markers. However, such attempts degrade the monodispersity and dispersion stability of the magnetic markers, and hence there is a risk of impairing the detection sensitivity and quantitative property of the magnetic biosensor.

On the other hand, in the detection method according to the present invention, the magnetic material is synthesized using as a template the gel particle to obtain the magnetic marker under a state in which the gel particle is bonded on the sensing element, and hence even in a case where the magnetic material content of each of the magnetic markers is enlarged, it is unnecessary for taking the dispersion stability thereof into consideration, thereby being capable of enhancing the detection sensitivity of the magnetic biosensor. Further, in a case if a gel particle having high size uniformity is used in advance, the magnetic marker having excellent monodispersity may be obtained, and thus the quantitative property of the magnetic biosensor may be enhanced.

Figure 2:
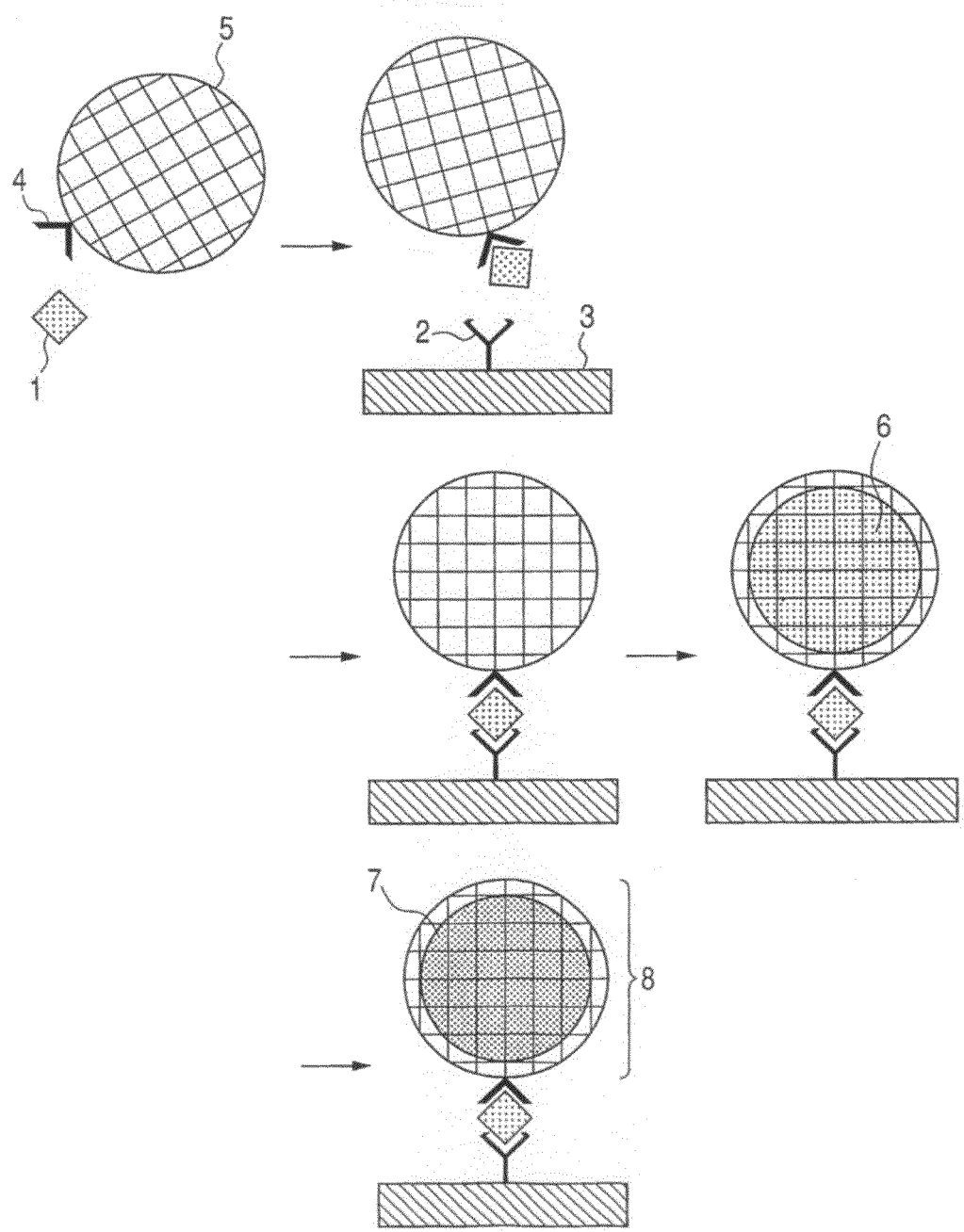
FIG. 2 is a schematic drawing illustrating a detection method according to the second mode of the present invention.

In a schematic drawing illustrated in FIG. 2, a detailed embodiment according to the second mode is described. In FIG. 2, after reaction of the target substance 1 and the second target substance trapping member 4 bonded on the gel particle 5 in the sample solution, the first target substance trapping member 2 bonded on the sensing element 3 is reacted with the target substance 1 bonded on the second target substance trapping member 4. Next, the magnetic material precursor 6 is charged into the sample solution to cause the gel particle 5 to absorb the magnetic material precursor 6. In addition, a magnetic material 7 is synthesized from the magnetic material precursor 6 to obtain the magnetic marker 8 including the gel particle 5 and the magnetic material 7. Finally, the magnetic marker 8 is magnetically detected with the sensing element 3.

Even in the detection method according to the second mode, there may be obtained the same effect as in the detection method according to the first mode.

A kit according to the present invention, for magnetically detecting the target substance in the sample solution, includes at least the following materials (1) to (3).

(1) A sensing element on which the first target substance trapping member is immobilized (2) A gel particle on which the second target substance trapping member is immobilized (3) A magnetic material precursor As the magnetic material precursor, one, which is absorbed into the gel particle to be held through interaction in a reaction solution, is used.

<Gel Particle>

The gel particle in the present invention is preferably a hydrogel particle. The hydrogel is generally defined as a swelling state in which a three-dimensionally cross-linked polymer net contains large amount of water. However, in the present invention, the hydrogel shall mean, in a broader sense, an aggregate of hydrophilic polymer containing large amount of water.

The gel particle of the present invention has an ability of absorbing a magnetic material precursor described later in a solution conducting reaction of the sample solution, etc. For that purpose, some kind of interaction must be acted on the gel particle and the magnetic material precursor. As the interaction, for example, a conventionally known interaction such as electrostatic interactions, hydrophobic interaction, or hydrogen bond may be applied, and in particular the object of the present invention may be achieved satisfactory in the case of the electrostatic interactions.

In order to act the electrostatic interactions on the gel particle and the magnetic material precursor, in a case where the magnetic material precursor is positively charged, the gel particle has a negative charge, and in a case where the magnetic material precursor is negatively charged, the gel particle has a positive charge.

As a method of imparting a negative charge to the gel particle, for example, there is a method involving bearing on the gel particle a charged functional group such as a carboxyl group, a sulfonic group, or a phosphate group, which dissociates in a water solution and exhibits a negative charge. On the other hand, as a method of imparting a positive charge to the gel particle, there is employed a method involving bearing on the gel particle the charged functional group such as amines, which dissociate in a water solution and exhibits a positive charge. However, the charged functional group in the present invention is not limited thereto, but any charged functional group may be applied as long as being capable of attaining the object of the present invention.

In order to achieve the magnetic biosensor with excellent quantitative property, the magnetic marker must be superior in monodispersity as much as possible. Therefore, in the present invention, the monodispersity is also required for the gel particle, which becomes a template of the magnetic marker. Specifically, it is preferred that a ratio (Dw/Dn) of a weight average particle diameter Dw) and a number average particle diameter (Dn) of the gel particle be 1.1 or less.

The Dw of the gel particle is not particularly limited, but is preferably 50 nm or more and less than 300 nm. In a case where the Dw is smaller than 50 nm, the saturated magnetization of each of the magnetic markers synthesized using as a template the gel particle does not exhibit a sufficient magnitude, and hence it is impossible to obtain a sufficient detection sensitivity in the magnetic biosensor. Further, in a case where the Dw is 300 nm or more, mobility of the gel particle is lowered, and hence there raise concerns of considerable lowering of a detection speed in the magnetic biosensor.

Further, it is preferred that the gel particle of the present invention be set to have an average aspect ratio (length/breadth) within a range of from 1.0 to 1.5, more preferably, from 1.0 to 1.2, thereby enhancing sphericity of the gel particle. The gel particle having the sphericity described above is advantageous because exhibiting an excellent flowability in a case where the gel particles are used by dispersing in a liquid, for instance.

<Magnetic Material and Magnetic Material Precursor>

The magnetic material in the present invention may be arbitrary selected depending on its purpose. However, it is preferred to use a magnetic material having magnetization (residual magnetization), when imparting a strong magnetic field of 5,000 oersted to the magnetic material and then returned to a zero magnetic field, becomes one third or less of the magnetization (saturated magnetization), when imparting the magnetic field of 5,000 oersted. As the magnetic material described above, various ferrite group such as a ferrosoferric oxide ($Fe_3O_4$), or maghemite ($\gamma$-$Fe_2O_3$); a metal such as iron, manganese, or cobalt, or alloys thereof may be exemplified.

In the magnetic biosensor, the magnetic marker having high saturated magnetization tends to be required, and hence the magnetic marker, which is classified into a strong magnetic material in a bulk state, is preferred. Judging from the above-mentioned views, the ferrite group is more preferred, and $Fe_3O_4$ (magnetite) is particularly preferred. However, the kinds of the magnetic materials are not limited as long as being capable of attaining the object of the present invention.

Further, the magnetic material precursor in the present invention is, for example, a substance which becomes a material for synthesis to obtain the magnetic material described above, and constitutes at least a part of the magnetic material.

The magnetic material precursor is charged into a liquid for conducting a reaction such as sample liquid, and is brought into contact with the gel particle which is held on the sensing element, thereby being absorbed into the gel particle. As a result, the magnetic material precursor is required to have the gel particle, interaction such as electrostatic interactions, hydrophobic interaction, or hydrogen bond. In a case where the gel particle has a negative charge, in order to act the electrostatic interactions, it is preferred to use the magnetic material precursor, which charges into positive in the reaction liquid. For example, among the metals such as iron, manganese, and cobalt, which are exemplified as the materials for the magnetic material, a metal salt, which dissolves in the reaction liquid and becomes a metal cation, may be suitably used.

The present invention may be implemented more preferably in a case where the magnetic material precursor is water soluble. As the method of synthesizing the magnetic material from the magnetic material precursor, there may be employed a conventionally known synthesis method which is selected depending on the magnetic material, and a combination of the precursors of the magnetic material.

<Target Substance Trapping Member>

The target substance trapping member in the present invention is a substance which affects a selection of the target substance in the sample solution, and includes, for example, a substance selectively and directly reacts with the target substance in the sample solution (so-called receptor), a substance which affects a reaction of the target substance (for example, substance selectively effecting catalytic action to reaction of target substance), or the like. Further, the trapping member may also serve a function relating to indications of the presence or absence and degree of detection, for example, a function of developing color in reaction with a substance released by the receptor and a residual substance. As the target substance trapping member used in the present invention, an enzyme, sugar chain, catalyst, antibody, antibody fragment, antigen, nucleic acid, and the like may be exemplified, but is not limited thereto.

The target substance trapping member is provided to each of the sensing element and the gel particle, and the one which is provided to the sensing element is defined as the first target substance trapping member, and the one provided to the gel particle is defined as the second target substance trapping member. Any member may be used for the first target substance trapping member and the second target substance trapping member as long as being capable of bonding with each other through intermediation of the target substance. Preferably, the respective members be bonded by capturing spatially different areas of the target substance.

<Target Substance>

The target substance of the present invention is a substance to be a detection subject, and is a substance selectively reacts directly with the target substance trapping member, a substance which affects the reaction of the target substance trapping member (for example, substance selectively effecting catalytic action on the reaction of the target substance trapping member), or the like. The target substance is not limited to a living substance, and also its size is not limited. However, in a case where the target substance is a living substance contained in a living organism such as a sugar, protein, amino acid, antibody, antigen and quasi-antigen, vitamin, and nucleic acid, its related substances, and a quasi-living substance artificially synthesized, the object of the present invention may be achieved satisfactory.

<Method of Bonding Target Substance Trapping Member to Gel Particle>

In the present invention, as long as being free from inhibiting the bonding ability of the target substance trapping member to the target substance, a bonding position of the target substance trapping member to the gel particle and a bonding method are not particularly limited. For example, in a case where the target substance trapping member is a protein, the bonding with the gel particle may be made at its carboxyl terminal or/and amino terminal, and as long as being free from inhibiting the functions of the target substance trapping member, the bonding with the gel particle may be made at a random position. Further, as an example of a method of bonding the trapping member to the gel particle, there may be exemplified methods such as physical adsorption and chemical bonding.

As for the physical adsorption of the target substance trapping member to the gel particle, the gel particle and the target substance trapping member may be nonspecifically adsorbed by mixing them in advance, which is preferred from a viewpoint of operation easiness. On the other hand, as a method of bonding the target substance trapping member to the gel particle, chemical bonding such as covalent bonding may be utilized. The chemical bonding is preferably used because the chemical bonding is strong in bonding than the physical adsorption. As a method of immobilizing in a covalent bonding manner the target substance trapping member to the gel particle, for example, in the case where the target substance trapping member is a protein, there is given a method involving reacting by a conventionally known method an amino group of an amino acid included in a protein sequence and a carboxyl group which is imparted to the gel particle as the charged functional group.

<Magnetic Marker>

The magnetic marker in the present invention is a composite particle including the gel particle and the magnetic material. The gel particle and magnetic material in the present invention are as described above.

<Magnetic Marker Precursor>

According to the present invention, the magnetic marker precursor is a composite particle including the gel particle and the magnetic material precursor. According to the present invention, the gel particle and the magnetic material precursor are as described above.

<Detection System>

The detection system using the magnetic biosensor of the present invention may be any type of method, as long as being a magnetic detection system capable of detecting the presence or absence of, or a concentration of the target substance in the sample solution by detecting the presence or absence of, or the number of the magnetic markers locating in the vicinity of the surface of the sensor device. Among others, the method utilizing a magnetic field effect is preferred, in particular, a magneto-resistance effect device, a hall effect device, a magnetic impedance device, a fluxgate device, or a superconducting quantum interference device may suitably be used.

EXAMPLES

Example 1

Production of Gel Particle A

As the second target substance trapping member, a gel particle A bonding an anti-lysozyme antibody is synthesized.

<Synthesis of Gel Particle>

0.2 g of N-isopropylacrylamide, 2.2 g of glycidylmethacrylate, and 0.06 g of methylenebisacrylamide are dissolved into 100 g of distilled water, and are subjected to nitrogen substitution for 30 minutes by nitrogen bubbling. After raising a temperature of this mixture to 70° C., 0.06 g of 2,2-azobis(2-aminopropane) hydrochloride (hereinafter referred to as V-50) is charged to conduct polymerization to obtain the gel particle. After purification by centrifugation, evaluation was conducted with DLS 8000 (manufactured by Otsuka Electronics Co., Ltd.), and it was confirmed that Dw is 182 nm, and Dw/Dn is 1.03.

<Addition of Carboxyl Group>

To a mercaptoacetic acid solution, the gel particle is added, and the resultant is subjected to reaction at room temperature, at pH 9 for 20 hours, thereby obtaining a gel particle having a carboxyl group. After purification by centrifugation, evaluation was conducted with DLS 8000 (manufactured by Otsuka Electronics Co., Ltd.), and it was confirmed that Dw is 235 nm, and Dw/Dn is 1.03.

<Immobilization of Anti-Lysozyme Antibody>

The gel particle is dispersed into a solution, in which 1-ethyl-3-(3-dimethylaminopropyl) carbodiimide hydrochloride and hydroxysuccinic acid imide are dissolved, and further anti-lysozyme (Rabbit-Poly) dissolved in a phosphate buffer solution is added thereto, the carboxyl group of the gel particle and the amino group of anti-lysozyme (Rabbit-Poly) are subjected to reaction. Herewith, the gel particle A on which anti-lysozyme (Rabbit-Poly) is bonded, is obtained.

Example 2

Production of Gel Particle B

Gel particle B, which has a sulfonic group as the charged functional group, and is bonded with an anti-lysozyme antibody as the second target substance trapping member, is synthesized.

<Synthesize of Gel Particle>

The gel particle is synthesized in the same manner as in Example 1.

<Addition of Sulfonic Group and Carboxyl Group>

To a solution in which 3-mercapto-1-propanesulfonic acid sodium and a mercaptoacetic acid are dissolved, the gel particle is added, and the resultant is subjected to reaction at room temperature, at pH 9 for 20 hours, thereby obtaining the gel particle to which the sulfonic acid group and the carboxyl group are added. After purification by centrifugation, evaluation was conducted with DLS 8000 (manufactured by Otsuka Electronics Co., Ltd.), and it was confirmed that Dw is 272 nm, and Dw/Dn is 1.04.

<Immobilization of Anti-Lysozyme Antibody>

The gel particle is dispersed in a solution in which 1-ethl-3-(3-dimethylaminopropyl) carbodiimide hydrochloride and hydroxysuccinic acid imide are dissolved, and further anti-lysozyme (Rabbit-Poly) dissolved in phosphate buffer solution is added thereto, the carboxyl group of the gel particle and the amino group of anti-lysozyme (Rabbit-Poly) are subjected to reaction. With this, the gel particle B having a sulfonic acid anti-lysozyme (Rabbit-Poly) is bonded, is obtained.

Example 3

Production of Sensing Element

The sensing device including a sensing element on which the first target substance trapping member is bonded, is produced as described below. Note that, in this example, as the detecting system, there is used a magneto-resistance effect device.

Figure 3A:
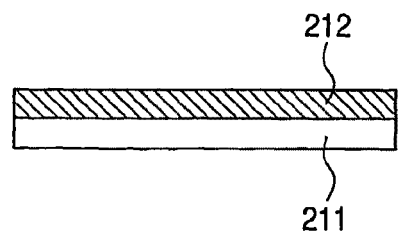
FIGS. 3A, 3B, 3C, 3D, 3E, 3F and 3G are schematic drawings illustrating a manufacturing process of a magnetic resistance device used in examples of the present invention.
Figure 3B:
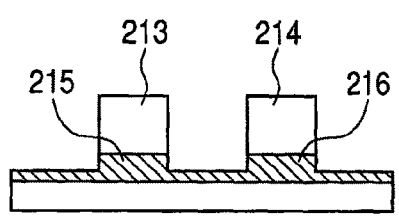
Figure 3C:
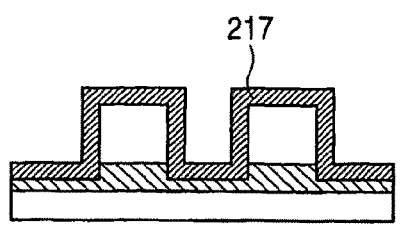
Figure 3D:
Figure 3E:
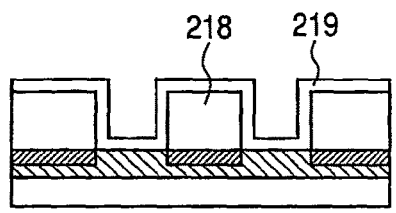
Figure 3F:
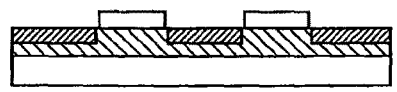
Figure 3G:
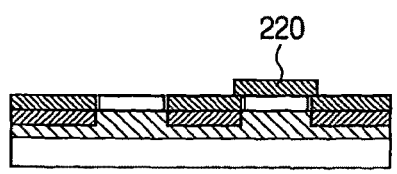

The magneto-resistance effect device of this example is produced by the following process. On a silicon wafer 211, a magnetic resistance effect film 212 formed of Ta (30 nm)/PtMn (20 nm)/CoFe (2 nm)/Ru (0.8 nm)/CoFe (2 nm)/AlOx (1.6 nm)/CoFe (3 nm)/Ru (5 nm)/Au (5 nm) is formed (FIG. 3A). The resist mask patterns 213 and 214 are formed on regions that become the sensing element 215 and the reference device 216, and through reactive ion etching, peripheries of the sensing element 215 and the reference device 216 are etched. The sensing element 215 and the reference device 216 are configured to have the same shape. The etching is controlled so that the etching is stopped at the AlOx film, and a metal film below the AlOx film is left as it is to function as a lower electrode (FIG. 3B). After etching, an SiN insulating film (14 nm) 217 is formed as the interlayer insulating film (FIG. 3C). The insulating film, which is formed on the sensing element 215 and the reference device 216, is subjected to grinding by polishing, and then the resist mask patterns 213 and 214 are dissolved by a solvent, tops of the sensing element 215 and the reference device 216 are opened (FIG. 3D). For formation of upper electrodes, the resist mask pattern 218 is formed, and then an Au film (20 nm) 219 is formed (FIG. 3E). Unnecessary Au film and resist mask patterns are subjected to lift off by using a solvent, and then the upper electrodes are formed (FIG. 3F). In addition, in order to cover the electrode surfaces except the tops of the sensing element, after the formation of the resist mask pattern, an SiN film (20 nm) 220 is formed, thereby conducting the lift off (FIG. 3G).

Figure 4:
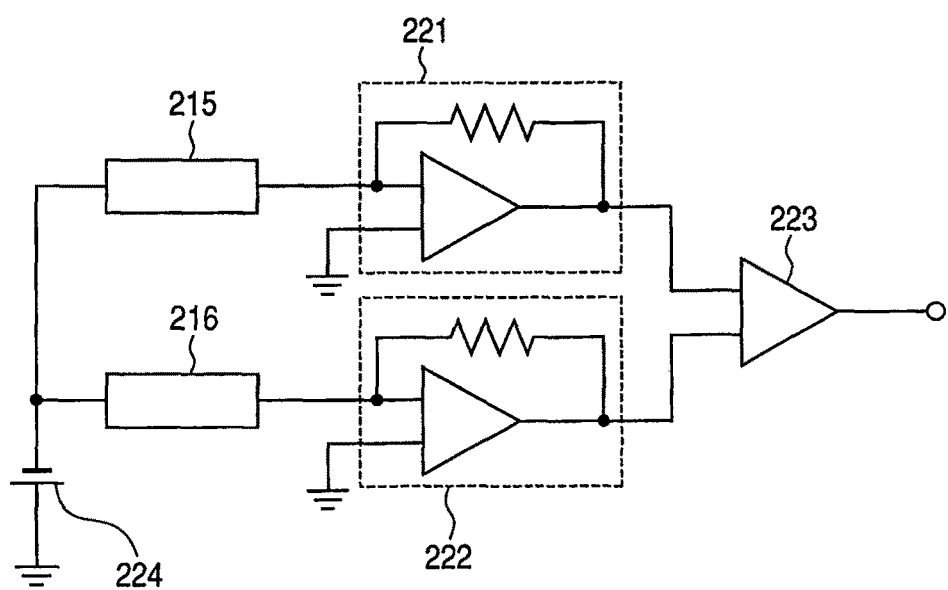
FIG. 4 is a schematic drawing of a detection circuit used in the examples of the present invention.

The sensing element 215 and the reference device 216 are electrically connected in parallel, so that voltages having the same magnitude are applied thereto. A current flowing from a DC power source 224 to the sensing element 215 and a current flowing to the reference device 216 each are converted into voltage values with I/V converters 221 and 222, and a voltage difference therebetween is output with a differential amplifier 223, thereby detecting presence or absence of, or a number of an antigen (target substance) (refer to FIG. 4).

In this example, the sensing device is configured by one sensing element. However through provision of a plurality of the sensing elements and sequential switching of the sensing elements with a selection transistor, it is possible to obtain detection signals of the respective sensor elements and to detect a plurality of antigen (target substance), or various kinds of the antigen (target substance).

Next, anti-lysozyme (Mouse-Mono) is bonded on the sensing element 215 (in FIG. 3G, Au film 219 surface) as the first target substance trapping member. First of all, an ethanol solution of 10-carboxy-1-decanethiol is applied to a detection area. With this operation, a carboxyl group is exposed to an Au film surface. Next, an N-hydroxysulfosuccinimide solution and 1-ethyl-3-(3-dimethylaminopropyl) carbodiimide hydrochloride solution are applied thereto in the same manner. With those operations, a succinimide group is exposed to Au film surface. The succinimide group and an amino group of the anti-lysozyme (Mouse-Mono) are subjected to reaction, thereby being capable of bonding the first target substance trapping member with the sensing element 215. Note that, non-reacted succinimide group on the Au film surface may be eliminated through an addition of hydroxylamine hydrochloride.

Example 4

Detection of Hen Egg-White Lysozyme (Gel Particle A)

In this example, hen egg-white lysozyme (HEL) is used as the target substance, the anti-lysozyme (Mouse-Mono) is used as the first target substance trapping member, and the anti-lysozyme (Rabbit-Poly) is used as the second target substance trapping member, the magnetic markers, which are obtained through the synthesis of the magnetic material by using as a template the gel particle A produced in Example 1, are magnetically detected.

Experimental operation is carried out in accordance with the following procedure.

1. The sensing device produced in Example 3 is immersed into a phosphate buffer solution containing HEL.
2. Non-reacted HEL is washed with the phosphate buffer solution.
3. The sensing device is immersed into the phosphate buffer solution in which the gel particle A is dispersed.
4. Non-reacted gel particle A is washed with the phosphate buffer solution.
5. The sensing device is immersed into distilled water.
6. The sensing device is immersed into an iron (II) chloride solution to cause the gel particle A to adsorb an iron ion.
7. Excessive iron ion is washed with water.
8. The solution is adjusted to pH 9 with an NaOH solution to synthesize magnetite.

Through the above-mentioned operation, HEL is captured by the anti-lysozyme (Mouse-Mono) and the anti-lysozyme (Rabbit-Poly), and further through the synthesis of the magnetic material using as a template the gel particle A, the magnetic markers are bonded on the sensing element as illustrated in FIG. 2. The magnetic detection of the presence or absence of the magnetic markers enables the detection of HEL as the target substance. Further, the plurality of magnetic markers bonded on the sensing element are excellent in monodispersity, and hence through the detection of the number of the magnetic markers, it is possible to determine the HEL contained in the sample liquid.

Example 5

Detection of Hen Egg-White Lysozyme (Gel Particle B)

Detection of hen egg-white lysozyme is conducted in the same manner as in Example 4 except for producing the magnetic markers which use the gel particle B produced in Example 2 as the template for synthesizing the magnetic material.

According to preferred embodiments of the present invention described above, there may be provided a detection method for enhancing the detection sensitivity and quantitative property of the magnetic biosensor for magnetically detecting the target substance in the sample solution.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-044422, filed Feb. 26, 2008, which is hereby incorporated by reference herein in its entirety.

The invention claimed is:

1. A detection method of detecting presence or absence of, or a concentration of a target substance in a sample solution through detection of presence or absence of, or a number of magnetic markers, comprising the steps of:
   (1) reacting the target substance in the sample solution with a first target substance trapping member immobilized on a sensing element and with a second target substance trapping member immobilized on a gel particle that does not comprise a magnetic material, and forming a composite material by bonding the first target substance trapping member and the second target substance trapping member through intermediation of the target substance, thereby holding the gel particle on the sensing element;
   (2) obtaining a magnetic marker precursor comprising the gel particle and a magnetic material precursor existing in the gel particle by bringing the magnetic material precursor into contact with the gel particle which is held on the sensing element through formation of the composite material;
   (3) synthesizing a magnetic material from the magnetic material precursor comprised in the magnetic marker precursor, thereby obtaining the magnetic markers comprising the gel particle and the magnetic material existing in the gel particle; and
   (4) detecting the presence or absence of, or the number of the magnetic markers with the sensing element.

2. The detection method according to claim 1, wherein the step (1) comprises the steps of:
   (1-I) reacting the target substance in the sample solution with the first target substance trapping member; and
   (1-ii) reacting the target substance bonded to the first target substance trapping member with the second target substance trapping member.

3. The detection method according to claim 1, wherein the step (1) comprises the steps of:
   (1-I) reacting the target substance in the sample solution with the second target substance trapping member; and
   (1-ii) reacting the target substance bonded to the second target substance trapping member with the first target substance trapping member.

4. The detection method according to claim 1, wherein the gel particle comprises a hydrogel particle.

5. The detection method according to claim 1, wherein the gel particle contains a charged functional group.

6. The detection method according to claim 5, wherein the charged functional group comprises a carboxyl group.

7. The detection method according to claim 5, wherein the charged functional group comprises a sulfonic group.

* * * * *